(12) United States Patent
Hsieh

(10) Patent No.: US 6,678,346 B2
(45) Date of Patent: Jan. 13, 2004

(54) CONE-BEAM CT SCANNER WITH IMAGE RECONSTRUCTION USING MULTIPLE SUB-IMAGES

(75) Inventor: Jiang Hsieh, Brookfield, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 294 days.

(21) Appl. No.: 09/975,543

(22) Filed: Oct. 11, 2001

(65) Prior Publication Data

US 2003/0073893 A1 Apr. 17, 2003

(51) Int. Cl.$^7$ .................................................. A61B 6/03
(52) U.S. Cl. ............................................. 378/4; 378/94
(58) Field of Search .............................. 378/4, 8, 15, 901

(56) References Cited

U.S. PATENT DOCUMENTS

| | | |
|---|---|---|
| 6,219,441 B1 | 4/2001 | Hu |
| 6,256,366 B1 * | 7/2001 | Lai ................................ 378/4 |
| 6,263,040 B1 | 7/2001 | Hsieh |
| 6,269,139 B1 | 7/2001 | Hsieh |

* cited by examiner

*Primary Examiner*—David V. Bruce
(74) *Attorney, Agent, or Firm*—George E. Haas; Quarles & Brady LLP

(57) ABSTRACT

A computed tomography imaging system includes a source of a conical beam of radiation and a two-dimensional detector array arranged on opposite sides of an axis of rotation. Projection data is acquired in a conventional manner as the source and detector array make a full rotation about an object. A conventional half-scan image reconstruction algorithm is applied to the projection data at a plurality of different center-view angles to produce a plurality of sub-images. Image segments, which are centered in each sub-image along the axis of the respective center-view angle, are selected and combined to form a cross-sectional image of the object. The regions of each sub-image preferably are defined by a weighting function.

20 Claims, 2 Drawing Sheets

CONE-BEAM CT SCANNER WITH IMAGE
RECONSTRUCTION USING MULTIPLE SUB-
IMAGES

CROSS-REFERENCE TO RELATED
APPLICATIONS

Not applicable.

STATEMENT REGARDING FEDERALLY
SPONSORED RESEARCH OR DEVELOPMENT

Not applicable.

BACKGROUND OF THE INVENTION

The present invention relates to computed tomography (CT) imaging apparatus; and more particularly, to the acquisition of data from the separate x-ray detectors in 2D detector arrays.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon a row, or one-dimensional array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered back-projection technique. This process converts the attenuation measurements from a scan into integers called "CT numbers" or "Hounsfield units", which are used to control the brightness of a corresponding pixel on a cathode ray tube display.

In one type of multi-slice CT imaging system 10 as shown in FIG. 1, the x-ray beam 14 also fans out along the z-axis producing a "cone-beam". The detectors 22 are arranged in a two dimensional array 20 that has multiple rows of detectors to acquire attenuation measurements in a plurality of slices disposed along the z axis. The backprojected slice image is reconstructed from the volumetric data using the Feldkamp algorithm.

The reconstructed volume for an axial scan is a cylindrically shaped region. FIG. 2 illustrates a cross sectional view of the volume coverage at the iso-channel plane (a plane passing through both the x-ray focal spot 16 and the detector iso-channels and parallel to the z-axis). The desired reconstructed volume is represented by a dashed rectangle 50, having a height D that is equal to the height of the detector at the iso-center along the z-axis. From an image reconstruction point-of-view, every voxel, or element, in the image needs to be sampled by all projections to ensure artifact free reconstruction. However, the volume that satisfies this condition is depicted by a cross-hatched hexagon 52. In practice, the reconstruction volume for each scan is limited to the thick line rectangle 54 enclosed inside the cross-hatched hexagon 52 in order to obtain a continuous reconstruction volume with multiple axial scans. As a result, the distance between the adjacent axial scans cannot be larger than the dimension of this inner rectangle along the along the z-axis.

If the distance from the source to iso-center is denoted by S and the radius of the reconstruction field of view (x-y) is denoted by R, the distance t between adjacent axial scans for continuous coverage is given by the expression:

$$t \leq \left(\frac{S-R}{S}\right)D \quad (1)$$

Thus, to obtain continuous coverage of an organ within the patient being scanned, the distance between adjacent scans is limited to about half of the detector coverage in the z-axis at the iso-center. This significantly reduces the volume coverage capability of the scanner. Therefore it is desirable to increase the reconstruction volume to the full distance D. However doing so necessitates extensive extrapolation of the projection data and thus introduces significant image artifacts because the stippled triangular areas 56 and 58 at each corner of the desired reconstruction volume 50 are not fully scanned. As seen in FIG. 2, when the emitter 12 and detector array 20 are oriented as illustrated, the corner areas 58 closest to the detector array are within the x-ray beam 14. However, in this orientation, the triangular corner areas 56 closest to the emitter 12 are outside the x-ray beam 14. When the emitter and detector assembly has rotated 180°, i.e. have reversed the illustrated positions, corner areas 58 are outside the x-ray beam and corner areas 56 lie within the beam. As a consequence, the triangular corner areas 56 and 58 are only partially scanned during a complete rotation of the emitter and detector array. This requires extrapolation of the data for these areas which generates artifacts in the reconstructed image.

Therefore, although it is desirable to increase the size of the reconstruction volume as much as possible, ideally to distance D, doing so with conventional processes introduces significant artifacts into the reconstructed image. As a consequence, an alternative reconstruction process which reduces such artifacts is desired.

SUMMARY OF THE INVENTION

A computed tomography imaging system, includes a source of a conical beam of radiation and a multi-row detector array arranged on opposite sides of an axis of rotation. That imaging system employs an image reconstruction method which comprises rotating the source and detector about the axis of rotation. While that rotating occurs, x-ray attenuation data samples are collected from the multi-row detector array at a plurality of projection angles β thereby producing a set of projection data.

A half-scan image reconstruction technique is applied to the set of projection data at a plurality of different center-view angles $β_0$ to produce a plurality of sub-images. The plurality of sub-images then are combined, such as by superimposition for example, to form a cross-sectional image of the object.

The preferred reconstruction technique includes weighting the set of projection data to produce a set of weighted data. For example, the weighting process applies a first weight to data samples within a first region centered about the respective center-view angle $\beta_0$. A second weight is applied to data samples within predefined second regions on either side of the first region. A third weight is applied to data samples in the remainder of the set of projection data. The weighted data is filtered using a conventional filter for single slice scans. The filtered data are backprojected by known 3-D backprojection algorithms to produce a plurality of sub-images which are then combined by weighting functions to formulate the final image.

BRIEF DESCRIPTION OF THE OF THE DRAWINGS

Figure 8:
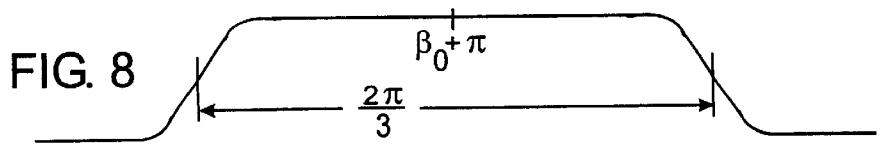

FIG. 8 graphically illustrates a weighting function employed in one techniques for producing a sub-image.

DETAILED DESCRIPTION OF THE INVENTION

Figure 1:
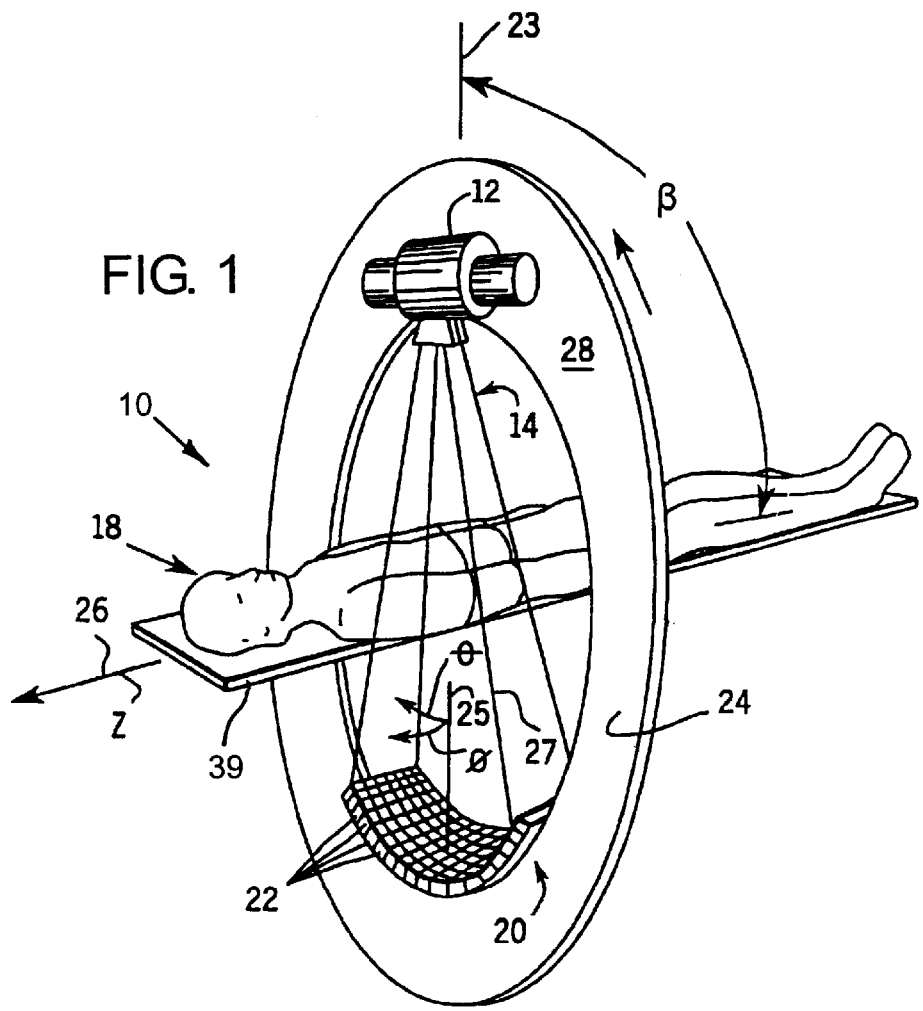
FIG. 1 is a pictorial view of a gantry of a CT imaging system.
Figure 3:
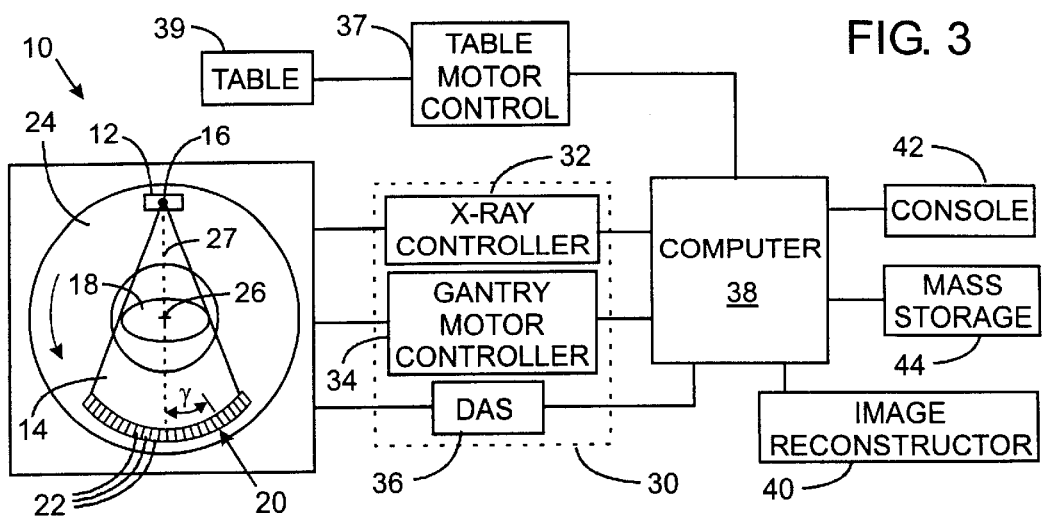
FIG. 3 is a block schematic diagram of a CT imaging system in which the present invention may be employed.

With reference to FIGS. 1 and 3, a CT imaging system 10 includes an x-ray source 12 oriented to project a cone beam of x-rays 14 from a focal spot 16 through a patient 18 to be received by a two-dimensional detector array 20. The two-dimensional detector array 20 includes a number of detector elements 22 arranged over the area of the detector array 20 in generally perpendicular columns and rows to detect a projected image of the x-rays 14 passing through the patient 18.

The x-ray source 12 and the two-dimensional detector array 20 are mounted on either side of a gantry 24 so as to rotate about an axis of rotation 26 generally positioned within the patient 18. The axis of rotation 26 forms the z-axis of a Cartesian coordinate system having its origin centered within the cone beam 14. The plane defined by the x and y axes of this coordinate system thus defines a plane of rotation, specifically the gantry plane 28 of the gantry 24.

Rotation of the gantry 24 is measured by angle $\beta$ from an arbitrary reference position within the gantry plane 28. Angle $\beta$ varies between 0 and $2\pi$ radians (360°). The x-rays of the cone beam 14 diverge from the gantry plane 28 by angle $\phi$ and diverge along the gantry plane 28 by angle $\phi$. The two-dimensional detector array 20 is arranged as a section of the surface of a sphere having a center at the focal spot 16, and its array of detector elements 22 is arranged to receive and make intensity measurements along the rays of the cone beam 14 throughout the angles of $\phi$ and $\theta$ of the cone beam 14. the detector array 20 is comprised of a 2D array of detector elements 22 arranged in rows which extend along an in-slice dimension. Each row may include, for example, 1,000 separate detector elements, and the array 20 may include 16 rows disposed along the slice dimension. The detectors 22 may be gas or, solid state detectors which produce an electrical signal proportional to the x-ray flux received over the sample period.

Referring to FIG. 3, the control subsystem of the CT imaging system 10 has gantry associated control modules 30 which include: x-ray controller 32, which provides power and timing signals to the x-ray source 12, gantry motor controller 34, which controls the rotational speed and position of the gantry 24. A data acquisition system (DAS) 36 receives projection data from the two-dimensional detector array 20 and converts the data into digital form for later computer processing, while preserving the values of $\phi$, $\theta$, and the gantry angle $\beta$ at which the data was taken. The x-ray controller 32, the gantry motor controller 34 and the data acquisition system 36 are connected to computer 38. The computer 38 also governs operation of a table motor control 37 which drives a motor that moves the patient table 39 along the z-axis 26.

The computer 38 is a general purpose minicomputer programmed to acquire and manipulate projection data as will be described in detail below. The computer 38 is connected to an image reconstructor 40 which performs high speed image reconstruction according to methods known in the art.

The computer 38 receives commands and scanning parameters via operator console 42 which is generally a CRT display and keyboard that enables an operator to enter parameters for the CT scan and to display the reconstructed image. A mass storage device 44 provides a means for storing operating programs.

During data acquisition, the CT imaging system 10 functions as a conventional cone-beam system in gathering data. Specifically, the table 39 is held stationary as the x-ray emitter 12 and detector array 20 make a complete revolution around the gantry 24 about the axis of rotation 26. At each of a plurality of angular positions $\beta$, the attenuation data from all the detectors 22 in array 20 are stored in the mass memory 44. Upon completion of a full rotation, the computer commands the table motor control 37 to advance the table 39 to another position along the z-axis 26 and another rotational scan of the patient 18 is preformed. This process is repeated until the desired portion of the patient 18 has been fully scanned.

Then image reconstruction commences. The essence of the present invention in the reconstruction of a plurality of sub-images each representing a wedge of the circular slice image. Each sub-image is produced using a half-scan reconstruction technique at a different center-view angle $\beta_0$ spaced around a full $2\pi$ radian rotation. Each sub-image comprises a wedge portion of the half-scan reconstructed image that contains the least amount of artifacts. The details of the present invention will be explained using an exemplary procedure that employs three sub-images produced at center-view angles of $\pi/3$ radians, $\pi$ radians, and $5\pi/3$ radians. However, a greater number of sub-images can be utilized with commensurately smaller intervals between the center-view angles. For example, four sub-images having $\pi/2$ radian wedges could be produced utilizing four center-view angles $\beta_0$ of 0, $\pi/2$, $\pi$, and $3\pi/2$ radians. The artifact reduction improves as the number of sub-images wedges increases, however, that also increases the amount of computation time to reconstruct the full slice image. The separate sub-images then are patched together to form the full slice image representing a cross section through the patient.

Figure 2:
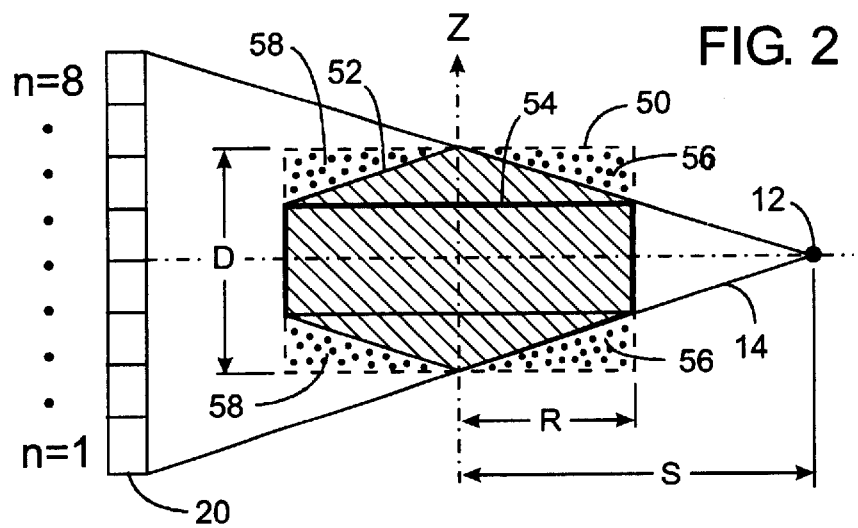
FIG. 2 illustrates the reduced volume coverage of a conventional cone-beam, multiple slice CT imaging system.
Figure 4:
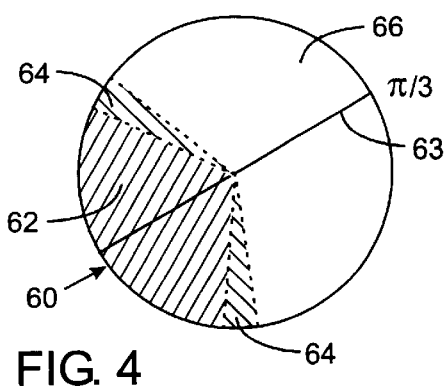
FIGS. 4, 5 and 6 depict three sub-images which are reconstructed according to the present invention.

With reference to FIG. 4, a first half-scan reconstruction is performed at the center-view angle $\beta_0=\pi/3$ radians. The projection data stored in mass storage 44 is weighted by the following function prior to filtering and application of the three-dimensional back-projection algorithm:

$$\theta_n(\gamma, \beta, \beta_o) =$$

$$\begin{cases} \dfrac{\beta - \beta_o + \pi/2 + \gamma_m}{2\gamma_m - 2\gamma} & \beta_o - \pi/2 - \gamma_m \le \beta < \beta_o - \pi/2 + \gamma_m - 2\gamma \\ 1, & \beta_o - \pi/2 + \gamma_m - 2\gamma \le \beta < \beta_o + \pi/2 - \gamma_m - 2\gamma \\ \dfrac{\beta_o + \pi/2 + \gamma_m - \beta}{2\gamma_m + 2\gamma} & \beta_o + \pi/2 - \gamma_m - 2\gamma \le \beta < \beta_o + \pi/2 + \gamma_m \\ 0, & \text{OTHERWISE} \end{cases}$$

$$w_n(\gamma, \beta, \beta_o) = 3\theta_n^2(\gamma, \beta, \beta_o) - 2\theta_n^3(\gamma, \beta, \beta_o)$$

where n is the detector row index (see FIG. 2), $\beta_O$ is the center-view angle of a half scan reconstruction, y is the angle between a given detector ray and the iso-ray 27 (a line from the x-ray focal spot 16 to the detector array 20 which passes through the axis of rotation 26, see FIG. 3), and β is the projection angle. The weighting of the projection data accounts for the greater likelihood of artifacts occurring the farther the data point is from the center-view angle. It will be understood that when other numbers of sub-images are employed, other weighting functions may be utilized. For example, helical interpolation or helical extrapolation algorithms developed for single slice CT can be utilized as weighting functions.

The weighted projection data is then filtered along the γ direction as is commonly done for single slice scans or for the Feldkamp reconstruction for a cone beam.

A three-dimension backprojection technique for a cone beam then is applied to the filtered projection data to create a first sub-image 60 depicted in FIG. 4. The first sub-image 60 has an approximately 2π/3 radian wedge shaped first primary segment 62 opposite the center-view angle and centered on the axis 63 of that view angle which passes through the iso-center, i.e. the center of the wedge is at angle $\beta_0+\pi$. The first primary segment 62 has a relatively minimal amount of artifacts and thus contains voxels which have not been attenuated by the weighting function. The image elements, or voxels, in smaller wedge shaped segments 64 on each side of the first primary segment 62 are attenuated by amounts that increase with increase in the angular distance from that first primary segment. Thus the image intensity in these smaller wedge segments 64 gradually decreases. The voxels in the remainder of the sub-image (the non-crosshatched portion 66) have been assigned a zero value by the weighting function.

There are two approaches which can be employed to produce the wedge shaped sub-image. The first is to use a conventional three-dimension backprojection technique to produce a full image representing the entire 2π slice region. Then another weighting function, depicted in FIG. 8, is applied to the full reconstructed image to suppress information that does not fall within the desired of the sub-image region. The weight applied to a given voxel is a function of the voxel's angular position in the image. The weighting function is centered opposite to the center-view angle, at angle $\beta_0+\pi$. A weight of one is applied to the voxels in the primary segment 62 and the weight decreases in the smaller border wedge segments 64 the farther the voxel is from the primary segment 62. A weight of zero is applied to voxels that are in region 66 in the full image.

The second approach produces a sub-image directly in the backprojection process. Here the backprojection is preformed only in a 2/3 π region corresponding to the sub-image area. Although this results in a more complex backprojection process, it could result in less computation as region 66 is not backprojected.

Figure 5:
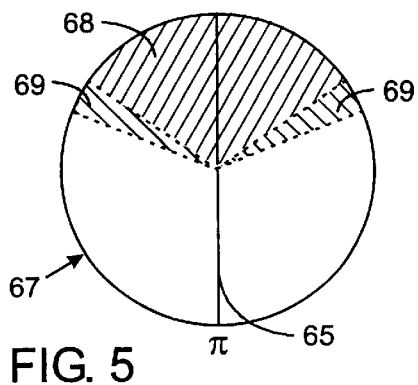

Next, this novel half-scan back projection process is applied a second time to the projection data using a center-view angle $\beta_0$ of π. The projection data is weighted, filtered and a second sub-image is reconstructed using the half-scan algorithm. The second sub-image 67, shown in FIG. 5, has a second primary segment 68 which has a wedge shape of approximately 2π/3 radians opposite to the center-view angle and centered on the axis 65 of that view angle. The image intensity of the voxels in the second primary segment has not been attenuated by the weighting function. The second primary segment 68 is flanked by a pair of smaller wedge shaped segments 69 in which the image intensity gradually decreases going away from the second primary segment.

Figure 6:
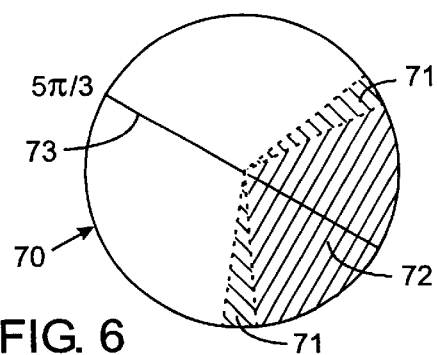

The half-scan back projection process is applied a third time to the stored projection data to produce a third sub-image 70 shown in FIG. 6 that is reconstructed at a center-view angle $B_0=5\pi/3$. The third sub-image 72 has a third primary segment 72 which is a 2π/3 radian wedge centered on the axis 73 of and opposite to the center-view angle. The image intensity of the voxels in the third primary segment has not been attenuated by the weighting function. The third primary segment 72 is flanked by a pair of smaller wedge shaped segments 71 in which the image intensity gradually decreases going away from the third primary segment. The weighting functions for the three sub-images have the property that the summation of the three functions is unity within the reconstruction region of interest.

Figure 7:
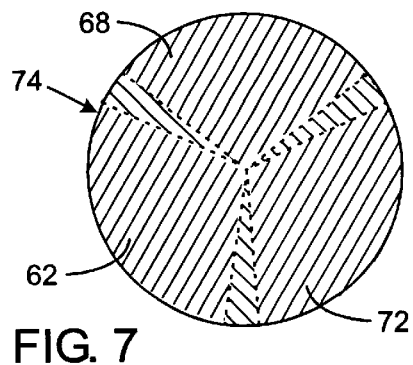
FIG. 7 depicts a full scan image which is assembled from the sub-images.

Once all three sub-images 60, 67 and 70 have been formed, the computer combines them to form the final full slice image 74 depicted in FIG. 7. In essence the three sub-images are superimposed over each other. Because of the manner in which the data was weighted, the result is as thought the primary segments 62, 68 and 72 were cropped and placed adjacent one another into the final full slice image. The superimposition overlays the smaller wedge segments 64, 69 and 71 which feathers the transition between the primary segments 62, 68 and 72.

It should be understood that the quality of each reconstructed sub-image is best at a location that corresponds to the iso-ray of the center-view. Image quality degrades gradually from that center line. Therefore, image quality will improve by using greater numbers of sub-images, each having a smaller wedge angle. For example, the image quality of the resultant image produced by five sub-images will be greater than that produced by three sub-images. However, this involves a trade-off between image quality and computation time.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. For example, instead of the half scan weights, helical weighting functions can be used to produce sub-images. In addition, the above scheme can be applied only to the image slices near the outer rows of the detector. For the regions that are close to the detector center plane, simple row interpolation can be used. Accordingly, the scope of the invention should be determined from the following claims and not limited by the above disclosure.

What is claimed is:

1. A method for producing cross-sectional image of an object by using a computed tomography imaging system, which includes a source of a conical beam of radiation and a multi-row detector array arranged on opposite sides of an axis of rotation, said method comprising:

rotating the source and detector array about the axis of rotation;

while rotating, collecting x-ray attenuation data samples from the multi-row detector array at a plurality of projection angles β to produce a set of projection data;

applying a projection weighting image reconstruction technique to the set of projection data at a plurality of different center-view angles $\beta_0$ to produce a plurality of sub-images; and combining the plurality of sub-images to form a cross-sectional image of the object.

2. The method as recited in claim 1 wherein the combining comprises superimposing the plurality of sub-images to form a cross-sectional image of the object.

3. The method as recited in claim 1 wherein producing each of the plurality of sub-images comprises:

applying a weighting function to the set of projection data to produce a set of resultant data; and processing the set of resultant data with an image reconstruction algorithm using a given center-view angle $\beta_0$.

4. The method as recited in claim 3 wherein the weighting function applies a first weight to data samples within a first group of the set of projection data centered about data samples on an axis of the given center-view angle $\beta_0$, applies a second weight to data samples within predefined second groups on each side of the first group, and applies a third weight to data samples in a remainder of the set of projection data.

5. The method as recited in claim 4 wherein the second weight for a given data sample varies as a function of a distance between the given data sample and the first group.

6. The method as recited in claim 3 wherein the weighting function is defined by the expression:

$$\theta_n(\gamma, \beta, \beta_o) = \begin{cases} \dfrac{\beta - \beta_o + \pi/2 + \gamma_m}{2\gamma_m - 2\gamma} & \beta_o - \pi/2 - \gamma_m \leq \beta < \beta_o - \pi/2 + \gamma_m - 2\gamma \\ 1, & \beta_o - \pi/2 + \gamma_m - 2\gamma \leq \beta < \beta_o + \pi/2 - \gamma_m - 2\gamma \\ \dfrac{\beta_o + \pi/2 + \gamma_m - \beta}{2\gamma_m + 2\gamma} & \beta_o + \pi/2 - \gamma_m - 2\gamma \leq \beta < \beta_o + \pi/2 + \gamma_m \\ 0, & \text{OTHERWISE} \end{cases}$$

where n designates a row of the multi-row detector array, $\beta_O$ is the center-view angle of a half scan reconstruction, γ is an angle between a given detector element and an iso-center axis, and β is a projection angle.

7. The method as recited in claim 1 wherein applying a projection weighting image reconstruction technique utilizes a half-scan image reconstruction algorithm.

8. The method as recited in claim 1 wherein applying a projection weighting image reconstruction technique produces each sub-image by creating a full slice image and selecting a region of the full slice image as the respective sub-image.

9. The method as recited in claim 1 wherein applying a projection weighting image reconstruction technique produces each sub-image by creating a full slice image containing image elements and selecting a group of the image elements to produce the respective sub-image.

10. The method as recited in claim 8 wherein the group of the image elements is selected by applying a weighting function to image elements of the full slice image.

11. The method as recited in claim 1 wherein producing each of the plurality of sub-images comprises:

applying a weighting function to the set of projection data to produce a set of weighted data;

filtering the weighted data to produce a set of filtered data; and backprojecting the set of filtered data with a three-dimension reconstruction algorithm.

12. A method for operating a computed tomography imaging system, which includes a source of a conical beam of radiation and a two-dimensional detector array arranged on opposite sides of an axis of rotation, said method comprising:

rotating the source and two-dimensional detector array about the axis of rotation;

while rotating, collecting x-ray attenuation data samples from the two-dimensional detector array during each one of a plurality of views of an object to produce a set of projection data;

creating an image segment by:
(a) applying a weighting function to the set of projection data to produce a set of resultant data; and
(b) processing the set of resultant data with a projection weighting reconstruction algorithm using a center-view angle $\beta_0$;

repeating steps (a) and (b) using different center-view angles to create a plurality of image segments; and combining the plurality of image segments to form a cross-sectional image of the object.

13. The method as recited in claim 12 wherein the weighting function applies a first weight to data samples within a first group centered about given center-view angle $\beta_0$, applies a variable weight to data samples within predefined second groups on either side of the first group, and applies a second weight to data samples in a remainder of the set of projection data.

14. The method as recited in claim 13 wherein the variable weight applied to data samples is a function of a distance between each data sample and the first group.

15. The method as recited in claim 14 wherein the data samples within the predefined second groups are weighted lesser amounts the farther a data sample is from an axis of the center-view angle $\beta_0$.

16. The method as recited in claim 12 further comprising filtering the resultant data before processing the set of resultant data with the projection weighting reconstruction algorithm.

17. The method as recited in claim 12 wherein the combining comprises placing the image segments adjacent each other to form a cross-sectional image of the object.

18. The method as recited in claim 12 wherein the combining comprises superimposing the plurality of sub-images to form a cross-sectional image of the object.

19. The method as recited in claim 12 wherein applying a projection weighting image reconstruction technique utilizes a half-scan image reconstruction algorithm.

20. The method as recited in claim 12 wherein applying a projection weighting image reconstruction technique produces each sub-image by creating a full slice image and selecting a region of the full slice image as the respective sub-image.

* * * * *